US010531926B2

(12) United States Patent
Roessler

(10) Patent No.: US 10,531,926 B2
(45) Date of Patent: Jan. 14, 2020

(54) SYSTEMS AND METHODS FOR IDENTIFYING AND TRACKING PHYSICAL OBJECTS DURING A ROBOTIC SURGICAL PROCEDURE

(71) Applicant: MAKO Surgical Corp., Ft. Lauderdale, FL (US)

(72) Inventor: Patrick Roessler, Merzhausen (DE)

(73) Assignee: MAKO Surgical Corp., Ft. Lauderdale, FL (US)

(*) Notice: Subject to any disclaimer, the term of this patent is extended or adjusted under 35 U.S.C. 154(b) by 298 days.

(21) Appl. No.: 15/602,621

(22) Filed: May 23, 2017

(65) Prior Publication Data
US 2017/0333137 A1  Nov. 23, 2017

Related U.S. Application Data

(60) Provisional application No. 62/340,176, filed on May 23, 2016.

(51) Int. Cl.
*A61B 34/20* (2016.01)
*A61B 34/10* (2016.01)
(Continued)

(52) U.S. Cl.
CPC .......... *A61B 34/20* (2016.02); *A61B 17/0206* (2013.01); *A61B 17/1703* (2013.01);
(Continued)

(58) Field of Classification Search
CPC .... A61B 2034/2055; A61B 2090/3983; A61B 2090/3937; A61B 6/12; A61B 2034/2065;
(Continued)

(56) References Cited

U.S. PATENT DOCUMENTS 5,603,318 A   2/1997  Heilbrun et al.
5,662,111 A   9/1997  Cosman
(Continued)

FOREIGN PATENT DOCUMENTS

WO   2004002352 A2   1/2004
WO   2007041267 A2   4/2007
(Continued)

OTHER PUBLICATIONS

International Search Report for Application No. PCT/US2017/033962 dated Sep. 4, 2017, 5 pages.
(Continued)

*Primary Examiner* — Aklilu K Woldemariam
(74) *Attorney, Agent, or Firm* — Howard & Howard Attorneys PLLC

(57) ABSTRACT

Navigation systems and methods for tracking physical objects near a target site during a surgical procedure. The navigation system comprises a robotic device and an instrument attached to the robotic device. A vision device is attached to the robotic device or the instrument and generates vision data sets. The vision data sets are captured from multiple perspectives of the physical object. A computing system associates a virtual object with the physical object based on one or more features of the physical object identifiable in the vision data sets. The virtual object at least partially defines a virtual boundary for the instrument.

28 Claims, 8 Drawing Sheets

(51) Int. Cl.
*A61B 34/30* (2016.01)
*A61B 17/02* (2006.01)
*A61B 17/17* (2006.01)
*B25J 9/16* (2006.01)
*A61B 34/00* (2016.01)

(52) U.S. Cl.
CPC .............. *A61B 34/10* (2016.02); *A61B 34/30* (2016.02); *B25J 9/1676* (2013.01); *B25J 9/1697* (2013.01); *A61B 34/76* (2016.02); *A61B 2034/102* (2016.02); *A61B 2034/105* (2016.02); *A61B 2034/107* (2016.02); *A61B 2034/207* (2016.02); *A61B 2034/2057* (2016.02); *A61B 2034/2065* (2016.02); *A61B 2034/2068* (2016.02); *A61B 2034/2072* (2016.02)

(58) Field of Classification Search
CPC ................ A61B 2090/365; A61B 5/06; A61B 2034/2063; A61B 90/90; A61B 6/547; A61B 1/0005; A61B 2017/00716; A61B 2034/2046; A61B 2090/064; A61B 2090/366; A61B 5/061; A61B 6/5247; A61B 5/107; A61B 6/4494; A61B 90/361; A61B 34/37; A61B 5/1076; A61B 34/10; A61B 2034/2048; A61B 2034/2068; A61B 2034/2072; A61B 34/20; A61B 34/30; A61B 17/0206; A61B 17/1703; A61B 2017/00734; A61B 2034/102; A61B 2034/105; A61B 2034/107; A61B 2034/2051; A61B 2034/2057; A61B 2034/2059; A61B 2034/207; A61B 2090/3612; A61B 2090/364; A61B 2090/3945; A61B 34/32; A61B 34/76; A61B 5/065; A61B 5/1122; A61B 34/25; A61B 90/03; G06T 2207/10012; G06T 7/33; G06T 7/73; G06T 7/246; G06T 2207/30241; H04N 13/279; H04N 2013/0092; G06K 2209/057; G06K 9/3241; G06K 9/00624; B25J 13/089; B25J 9/1676; B25J 9/1697; B25J 19/02; B25J 9/161; G05B 2219/39024; Y10S 901/01; Y02T 90/169; Y04S 30/14; G16H 10/60; G16H 50/70; G09B 23/28; G06F 3/016; G06F 3/04815; G06F 3/04845
USPC ........ 382/128, 130, 131, 264; 600/414, 407, 600/426, 424, 427, 417; 345/156, 634
See application file for complete search history.

(56) References Cited

U.S. PATENT DOCUMENTS

| | | | |
|---|---|---|---|
| 5,682,890 A | 11/1997 | Kormos et al. | |
| 5,732,703 A | 3/1998 | Kalfas et al. | |
| 5,921,992 A | 7/1999 | Costales et al. | |
| 6,165,181 A | 12/2000 | Heilbrun et al. | |
| 6,247,812 B1 * | 6/2001 | Miehle | A61B 3/10 351/206 |
| 6,484,049 B1 | 11/2002 | Seeley et al. | |
| 6,490,475 B1 | 12/2002 | Seeley et al. | |
| 6,675,040 B1 | 1/2004 | Cosman | |
| 6,968,224 B2 * | 11/2005 | Kessman | A61B 8/0841 128/916 |
| 7,155,316 B2 | 12/2006 | Sutherland et al. | |
| 7,623,250 B2 | 11/2009 | Moctezuma de la Barrera et al. | |
| 7,725,162 B2 | 5/2010 | Malackowski et al. | |
| 7,844,320 B2 | 11/2010 | Shahidi | |
| 8,116,848 B2 | 2/2012 | Shahidi | |
| 8,239,001 B2 * | 8/2012 | Verard | A61B 5/062 600/407 |
| 8,320,612 B2 | 11/2012 | Knobel et al. | |
| 8,601,380 B2 * | 12/2013 | Vaittinen | G06F 3/04815 715/757 |
| 8,792,963 B2 * | 7/2014 | Zhao | B25J 9/1689 600/424 |
| 9,008,757 B2 | 4/2015 | Wu | |
| 9,068,820 B2 | 6/2015 | Kosmecki et al. | |
| 9,119,655 B2 | 9/2015 | Bowling et al. | |
| 9,208,561 B2 | 12/2015 | Kruger et al. | |
| 2002/0082498 A1 | 6/2002 | Wendt et al. | |
| 2004/0111183 A1 | 6/2004 | Sutherland et al. | |
| 2007/0049819 A1 | 3/2007 | Stifter et al. | |
| 2008/0201016 A1 | 8/2008 | Finlay | |
| 2008/0208041 A1 | 8/2008 | Gilboa | |
| 2009/0088634 A1 * | 4/2009 | Zhao | B25J 9/1689 600/427 |
| 2010/0274389 A1 | 10/2010 | Ortmaier et al. | |
| 2011/0015521 A1 | 1/2011 | Faul | |
| 2012/0259204 A1 | 10/2012 | Carrat et al. | |
| 2013/0211421 A1 | 8/2013 | Abovitz et al. | |
| 2014/0180001 A1 | 6/2014 | von Grunberg et al. | |
| 2014/0200621 A1 | 7/2014 | Malackowski et al. | |
| 2014/0276943 A1 | 9/2014 | Bowling et al. | |
| 2014/0306866 A1 * | 10/2014 | Miller | G06T 19/006 345/8 |
| 2015/0018622 A1 * | 1/2015 | Tesar | A61B 1/05 600/202 |
| 2015/0265368 A1 * | 9/2015 | Chopra | A61B 5/062 600/424 |
| 2015/0265807 A1 * | 9/2015 | Park | A61M 25/0133 600/424 |
| 2016/0000518 A1 | 1/2016 | Thoranaghatte | |
| 2017/0172662 A1 * | 6/2017 | Panescu | A61B 90/37 |
| 2017/0177191 A1 * | 6/2017 | Lightcap | G06F 3/04815 |
| 2017/0189125 A1 * | 7/2017 | Malackowski | A61B 34/20 |
| 2018/0168740 A1 * | 6/2018 | Ryan | A61B 1/317 |

FOREIGN PATENT DOCUMENTS

| | | |
|---|---|---|
| WO | 2008002830 A2 | 1/2008 |
| WO | 2009045827 A2 | 4/2009 |
| WO | 2015024600 A1 | 2/2015 |
| WO | 2015086364 A1 | 6/2015 |
| WO | 2015172826 A1 | 11/2015 |
| WO | 2016154557 A1 | 9/2016 |

OTHER PUBLICATIONS

Microsoft, "Kinect Fusion", downloaded from https://www.msdn.microsoft.com/en-us/library/dn188670(d=printer).aspx on Feb. 26, 2016, pp. 1-9.

* cited by examiner

SYSTEMS AND METHODS FOR IDENTIFYING AND TRACKING PHYSICAL OBJECTS DURING A ROBOTIC SURGICAL PROCEDURE

RELATED APPLICATION

This application claims priority to and the benefit of U.S. Provisional Patent Application No. 62/340,176, filed on May 23, 2016, the entire disclosure and contents of which are hereby incorporated by reference herein.

TECHNICAL FIELD

The present disclosure relates generally to a system and method for identifying and tracking physical objects during a robotic surgical procedure.

BACKGROUND

Navigation systems assist users in precisely locating objects. For instance, navigation systems are used in industrial, aerospace, and medical applications. In the medical field, navigation systems assist surgeons in precisely placing surgical instruments relative to a target site in a patient. The target site usually requires some form of treatment, such as tissue removal. Conventional navigation systems employ a localizer that cooperates with trackers to provide position and/or orientation data associated with the surgical instrument and the target site, e.g., the volume of bone to be removed. The localizer is usually placed so that it has a field of view of the trackers. The trackers are fixed to the surgical instrument and to the patient to move in concert with the surgical instrument and the patient. The tracker attached to the patient is often attached to the bone being treated thereby maintaining a rigid relationship with respect to the target site owing to the rigid nature of the bone. By using separate trackers on the surgical instrument and the patient, the treatment end of the surgical instrument can be precisely positioned at the target site.

Often, retractors or other physical objects are located near the target site that should be avoided during the surgery. These retractors or other physical objects could be tracked in the same manner as the surgical instrument, e.g., using separate trackers, but adding trackers to the retractors and other physical objects can substantially increase costs and complexity in the navigation system, particularly by increasing the number of objects to be tracked by the localizer. Furthermore, since these physical objects are usually capable of movement relative to the trackers associated with the instrument and the patient, these additional physical objects aren't easily referenced to such trackers. It has been proposed to track these additional physical objects using object recognition techniques in images captured by a video camera attached to the localizer or otherwise fixed relative to the localizer. This approach, however, can be computationally expensive and difficult.

During robotic surgery, particularly when a robotic device is operating autonomously, avoidance of such physical objects is difficult when the navigation system is unable to identify the locations of all the physical objects near the target site. As a result, robotic devices are currently controlled to monitor for collisions with such physical objects and shut down in the event of a collision, relying, for instance, on feedback from a force/torque sensor to indicate a collision. However, waiting until a collision occurs before shutting down the robotic device is undesirable and results in damage to tools or the potential for endangering the patient with debris that may be created by such collisions, e.g., when rotary burs or saws hit retractors. Collisions with physical objects can delay the surgical procedure. Such delays can prolong the period in which patients are subjected to general anesthesia or otherwise increase risks associated with the surgical procedure.

Thus, there is a need in the art for systems and methods that address the identification and tracking of physical objects during robotic surgery.

SUMMARY

In one embodiment, a navigation system is provided for tracking a physical object near a target site during a surgical procedure. The navigation system comprises a robotic device and an instrument attachable to the robotic device. A vision device is attached to one of the robotic device or the instrument such that the vision device is movable with the robotic device. The vision device is configured to generate vision data sets. The vision data sets are captured from multiple perspectives of the physical object enabled by the vision device being moved in a plurality of degrees of freedom when moving the robotic device. A computing system is in communication with the vision device. The computing system has at least one processor configured to associate a virtual object with the physical object based on one or more features of the physical object identifiable in the vision data sets. The virtual object at least partially defines a virtual boundary for the instrument.

In yet another embodiment, a method for tracking a physical object is provided. The method comprises generating vision data sets in response to movement of the vision device resulting from movement of the robotic device. As a result of this movement, the vision data sets are captured from multiple perspectives of the physical object. The method further comprises associating a virtual object with the physical object based on one or more features of the physical object identifiable in the vision data sets. The virtual object defines a virtual boundary for the instrument.

This system and method provide several advantages. For instance, by moving the vision device relative to the physical object, which includes the one or more features, the computing system is able to both identify and locate the physical object and track movement of the instrument relative to the physical object. In some cases, a single vision data set (e.g., a single image) taken by the vision device may be sufficient to estimate a location of the physical object with subsequent vision data sets being useful to improve tracking results. This can be useful to avoid the physical object while treating a target site during a surgical procedure with the instrument. Additionally, by attaching the vision device to the moving robotic device or instrument, a lower cost vision device can be utilized that benefits from taking multiple vision data sets from different perspectives of the physical object, e.g., multiple video frames from different perspectives. As a result, such physical objects can be tracked without requiring separate, expensive trackers.

BRIEF DESCRIPTION OF THE DRAWINGS

Advantages will be readily appreciated as the same becomes better understood by reference to the following detailed description when considered in connection with the accompanying drawings.

DETAILED DESCRIPTION

Figure 1:
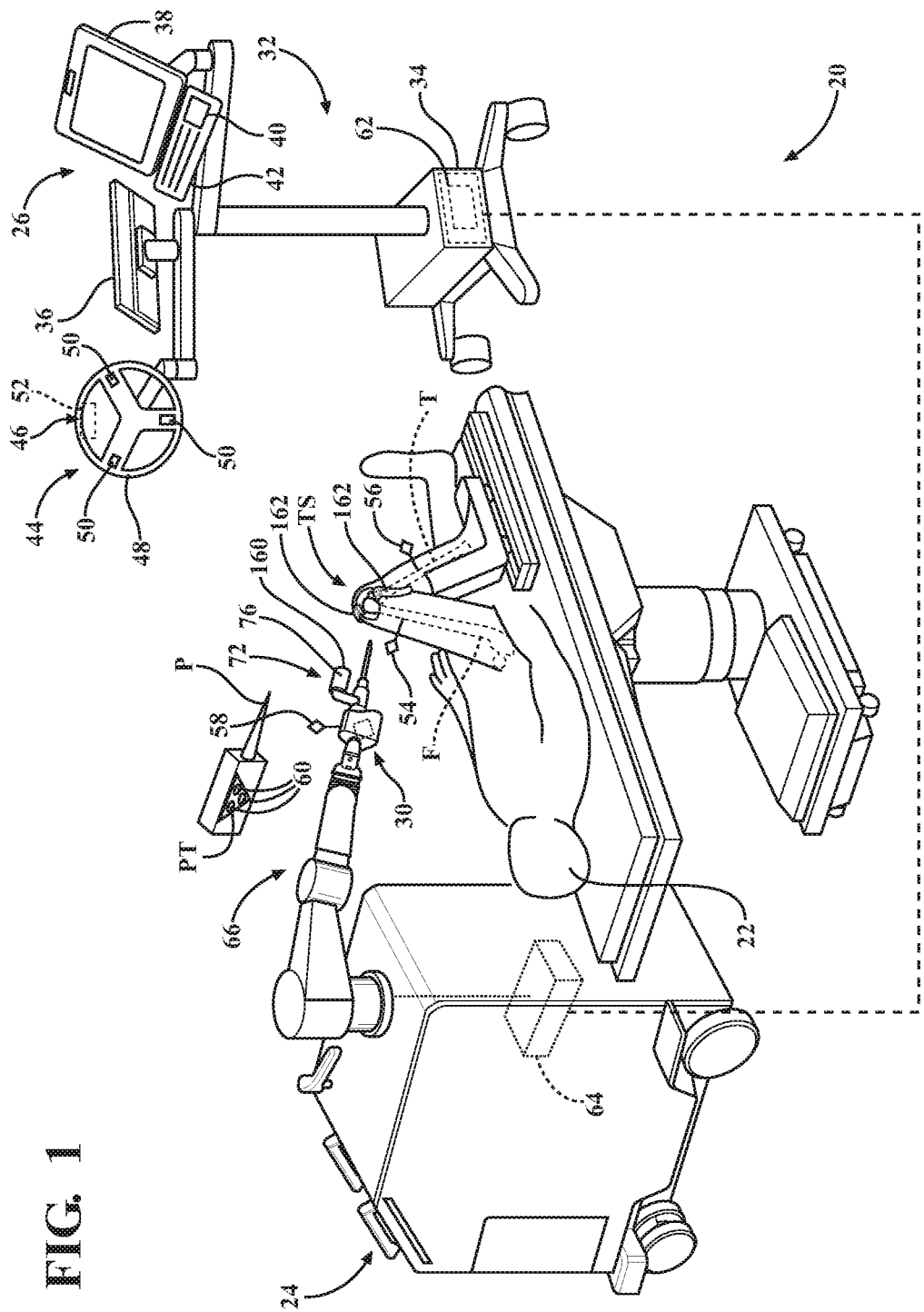
FIG. 1 is a perspective view of a robotic surgical system comprising a robotic device, a localizer, and a vision device.

As shown in FIG. 1, a system 20 for treating a patient 22 is illustrated. The system 20 is shown in a surgical setting such as an operating room of a medical facility. In the embodiment shown, the system 20 comprises a machining station 24 and a guidance station 26. The guidance station 26 is set up to track movement of various objects in the operating room. Such objects include, for example, a surgical instrument 30, a femur F of a patient, and a tibia T of the patient. The guidance station 26 tracks these objects for purposes of displaying their relative positions and orientations to a user and, in some cases, for purposes of controlling or constraining movement of the surgical instrument 30 relative to target sites, such as a femur target site TS. The surgical instrument 30 is shown as part of the machining station 24.

The guidance station 26 includes a navigation cart assembly 32 that houses a navigation computer 34. A navigation interface is in operative communication with the navigation computer 34. The navigation interface includes a first display 36 adapted to be situated outside of the sterile field and a second display 38 adapted to be situated inside the sterile field. The displays 36, 38 are adjustably mounted to the navigation cart assembly 32. First and second input devices 40, 42 such as a keyboard and mouse can be used to input information into the navigation computer 34 or otherwise select/control certain aspects of the navigation computer 34. Other input devices are contemplated including a touch screen (not shown) or voice-activation.

A localizer 44 communicates with the navigation computer 34. In the embodiment shown, the localizer 44 is an optical localizer and includes a localizer camera unit 46. The localizer camera unit 46 has an outer casing 48 that houses one or more optical position sensors 50. In some embodiments at least two optical sensors 50 are employed, preferably three or more. The optical sensors 50 may be three separate charge-coupled devices (CCD). In one embodiment three, one-dimensional CCDs are employed. It should be appreciated that in other embodiments, separate localizer camera units, each with a separate CCD, or two or more CCDs, could also be arranged around the operating room. The CCDs detect infrared signals. Additionally, the localizer 44 may employ different modalities and may be an electromagnetic localizer, RF localizer, ultrasound localizer, or any other conventional localizer capable of tracking objects.

The localizer camera unit 46 is mounted to an adjustable arm to position the optical sensors 50 with a field of view of the below discussed trackers that, ideally, is free from obstructions. In some embodiments the localizer camera unit 46 is adjustable in at least one degree of freedom by rotating about a rotational joint. In other embodiments, the localizer camera unit 46 is adjustable about two or more degrees of freedom.

The localizer camera unit 46 includes a localizer camera controller 52 in communication with the optical sensors 50 to receive signals from the optical sensors 50. The localizer camera controller 52 communicates with the navigation computer 34 through either a wired or wireless connection (not shown). One such connection may be an IEEE 1394 interface, which is a serial bus interface standard for high-speed communications and isochronous real-time data transfer. The connections could also use a company specific protocol. In other embodiments, the optical sensors 50 communicate directly with the navigation computer 34.

Position and orientation signals and/or data are transmitted to the navigation computer 34 for purposes of tracking objects. The navigation cart assembly 32, displays 36, 38, and localizer camera unit 46 may be like those described in U.S. Pat. No. 7,725,162 to Malackowski, et al. issued on May 25, 2010, entitled "Surgery System," hereby incorporated by reference.

Navigation computer 34 has the displays 36, 38, central processing unit (CPU) and/or other processors 62, memory (not shown), and storage (internal and external, not shown) necessary for carrying out the functions described herein. The navigation computer 34 is loaded with software as described below. The software converts the signals received from the localizer camera unit 46 into localizer data representative of the position and orientation of the objects being tracked by the localizer. The navigation computer 34 is capable of wired or wireless communication with a computer network (such as a Local Area Network (LAN) and/or the Internet). One or more data interfaces may be provided for the navigation computer 34 such as Universal Serial Bus (USB) interfaces or devices for reading data carriers such as CD-ROMs or SD cards. The internal storage or the external storage, or both, may be configured to store image data of a patient image taken by an imaging device. Alternatively, or in addition, such image data may also be received (e.g., downloaded) via the computer network. Moreover, the internal storage or the external storage, or both, may be configured to store various items of calibration data/information described herein. Such calibration data/information constitutes prior knowledge of the system 20, and various calibration data examples will be described below in more detail. As will be appreciated, the prior knowledge of the system 20 may alternatively, or in addition, comprise other items of information.

Guidance station 26 is operable with a plurality of tracking devices 54, 56, 58, also referred to herein as trackers. In the illustrated embodiment, one tracker is 54 is firmly affixed to the femur F of the patient and another tracker 56 is firmly affixed to the tibia T of the patient. Trackers 54, 56 are firmly affixed to sections of bone. Trackers 54, 56 may be attached to the femur F and tibia T in the manner shown in U.S. Pat. No. 7,725,162, hereby incorporated by references. Trackers 54, 56 could also be mounted like those shown in U.S. Patent Application Publication No. 2014/0200621, filed on Jan. 16, 2014, entitled, "Navigation Systems and Methods for Indicating and Reducing Line-of-Sight Errors," hereby incorporated by reference herein. In yet further embodiments, the trackers 54, 56 could be mounted to other tissues of the anatomy.

An instrument tracker 58 is firmly attached to the surgical instrument 30. The instrument tracker 58 may be integrated into the surgical instrument 30 during manufacture or may be separately mounted to the surgical instrument 30 in preparation for surgical procedures. A treatment end of the surgical instrument 30, which is being tracked by virtue of the instrument tracker 58, may comprise a rotating bur, electrical ablation tip, ultrasonic tip, sagittal saw blade, or other type of treatment element.

The trackers 54, 56, 58 can be battery powered with an internal battery or may have leads to receive power through the navigation computer 34, which, like the localizer camera unit 46, preferably receives external power.

In the embodiment shown, the surgical instrument 30 is attached to a manipulator 66 of the machining station 24. The manipulator 66 may also be referred to as a robotic device or a robotic arm. Such an arrangement is shown in U.S. Pat. No. 9,119,655, entitled, "Surgical Manipulator Capable of Controlling a Surgical Instrument in Multiple Modes," the disclosure of which is hereby incorporated by reference. The surgical instrument 30 may be any surgical instrument (also referred to as a tool) that is useful in performing medical/surgical procedures. The surgical instrument 30 may be a burring instrument, an electrosurgical instrument, an ultrasonic instrument, a reamer, an impactor, a sagittal saw, or other instrument. In some embodiments, multiple surgical instruments are employed to treat the patient, with each being separately tracked by the localizer 44.

The optical sensors 50 of the localizer 44 receive light signals from the trackers 54, 56, 58. In the illustrated embodiment, the trackers 54, 56, 58 are active trackers. In this embodiment, each tracker 54, 56, 58 has at least three active tracking elements or markers for transmitting light signals to the optical sensors 50. The active markers can be, for example, light emitting diodes or LEDs 60 transmitting light, such as infrared light. The optical sensors 50 preferably have sampling rates of 100 Hz or more, more preferably 300 Hz or more, and most preferably 500 Hz or more. In some embodiments, the optical sensors 50 have sampling rates of 8000 Hz. The sampling rate is the rate at which the optical sensors 50 receive light signals from sequentially fired LEDs 60. In some embodiments, the light signals from the LEDs 60 are fired at different rates for each tracker 54, 56, 58.

Figure 2:
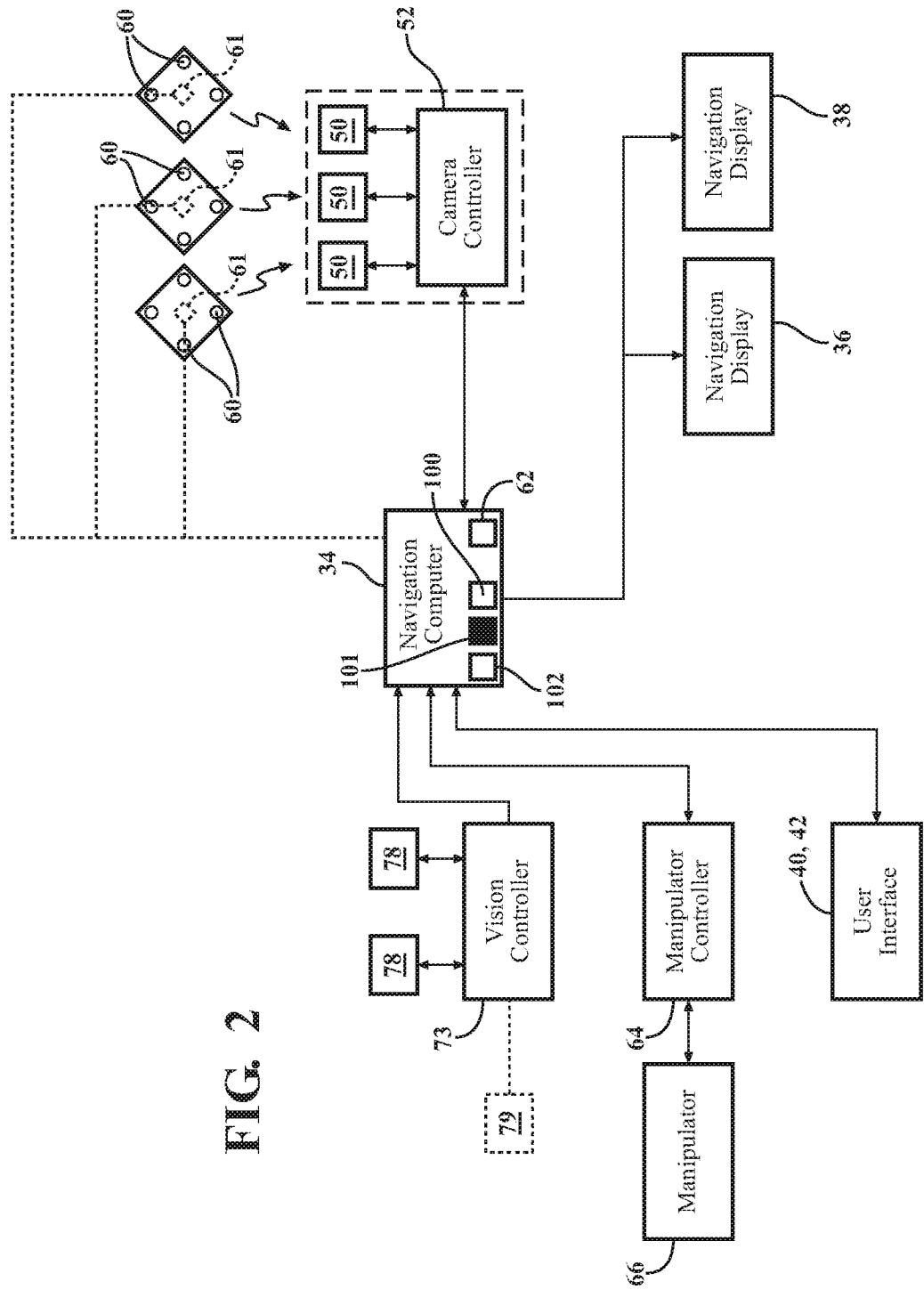
FIG. 2 is a schematic view of a control system for controlling the robotic surgical system.

Referring to FIG. 2, each of the LEDs 60 are connected to a tracker controller 61 located in a housing of the associated tracker 54, 56, 58 that transmits/receives data to/from the navigation computer 34. In one embodiment, the tracker controllers 61 transmit data on the order of several Megabytes/second through wired connections with the navigation computer 34. In other embodiments, a wireless connection may be used. In these embodiments, the navigation computer 34 has a transceiver (not shown) to receive data from the tracker controller 61.

In other embodiments, the trackers 54, 56, 58 may have passive markers (not shown), such as reflectors that reflect light emitted from the localizer camera unit 46. The reflected light is then received by the optical sensors 50. Active and passive arrangements are well known in the art.

In some embodiments, the trackers 54, 56, 58 also include a gyroscope sensor and accelerometer, such as the trackers shown in U.S. Pat. No. 9,008,757 to Wu, issued on Apr. 14, 2015, entitled "Navigation System Including Optical and Non-Optical Sensors," hereby incorporated by reference.

The navigation computer 34 includes the navigation processor 62. It should be understood that the navigation processor 62 could include one or more processors to control operation of the navigation computer 34. The processors can be any type of microprocessor or multi-processor system. The term processor is not intended to limit the scope of any embodiment to a single processor.

The localizer camera unit 46 receives optical signals from the LEDs 60 of the trackers 54, 56, 58 and outputs to the navigation processor 62 signals relating to the position of the LEDs 60 of the trackers 54, 56, 58 relative to the localizer 44. Based on the received optical (and non-optical signals in some embodiments), navigation processor 62 generates data indicating the relative positions and orientations of the trackers 54, 56, 58 relative to the localizer 44, such as through known triangulation methods. In some embodiments, the data is generated by the localizer camera controller 52 and then transmitted to the navigation computer 34.

Prior to the start of the surgical procedure, additional data are loaded into the navigation processor 62. Based on the position and orientation of the trackers 54, 56, 58 and the previously loaded data, navigation processor 62 determines the position of the treatment end of the surgical instrument 30 (e.g., the centroid of a surgical bur) and the orientation of the surgical instrument 30 relative to the target sites against which the treatment end is to be applied, such as the femur target site TS. In some embodiments, navigation processor 62 forwards these data to a manipulator controller 64. The manipulator controller 64 can then use the data to control the manipulator 66 as described in U.S. Pat. No. 9,119,655, entitled, "Surgical Manipulator Capable of Controlling a Surgical Instrument in Multiple Modes," the disclosure of which is hereby incorporated by reference. In one embodiment, the manipulator 66 is controlled to stay within virtual boundaries set by the surgeon. In the embodiment described herein, one such virtual boundary defines the volume of material of the femur F to be removed by the surgical instrument 30. Thus, the virtual boundary is a boundary for the treatment end of the surgical instrument 30 to stay within. The manipulator 66 can be controlled to operate in a manual mode of operation in which the user grasps and manipulates the instrument 30 to cause movement of the instrument 30 or autonomously, as described in U.S. Pat. No. 9,119,655, entitled, "Surgical Manipulator Capable of Controlling a Surgical Instrument in Multiple Modes," hereby incorporated by reference.

The navigation processor 62 also generates image signals that indicate the relative position of the treatment end to the target sites. These image signals are applied to the displays 36, 38. Displays 36, 38, based on these signals, generate images that allow the surgeon and staff to virtually view the relative position of the treatment end to the target sites. In most cases, the images illustrate the treatment end with respect to one target site at a time. For instance, in a surgical procedure in which the femur F and the tibia T are both being treated, the femur target site TS and the relative position of the treatment end of the surgical instrument 30 to the femur target site TS may be visually illustrated while material is being removed from the femur F. Likewise, when the user is finished removing material from the femur F and is ready to remove material from the tibia T, the display 36, 38 may only illustrate placement of the treatment end of the surgical instrument 30 with respect to the target site associated with the tibia T.

Figure 3:
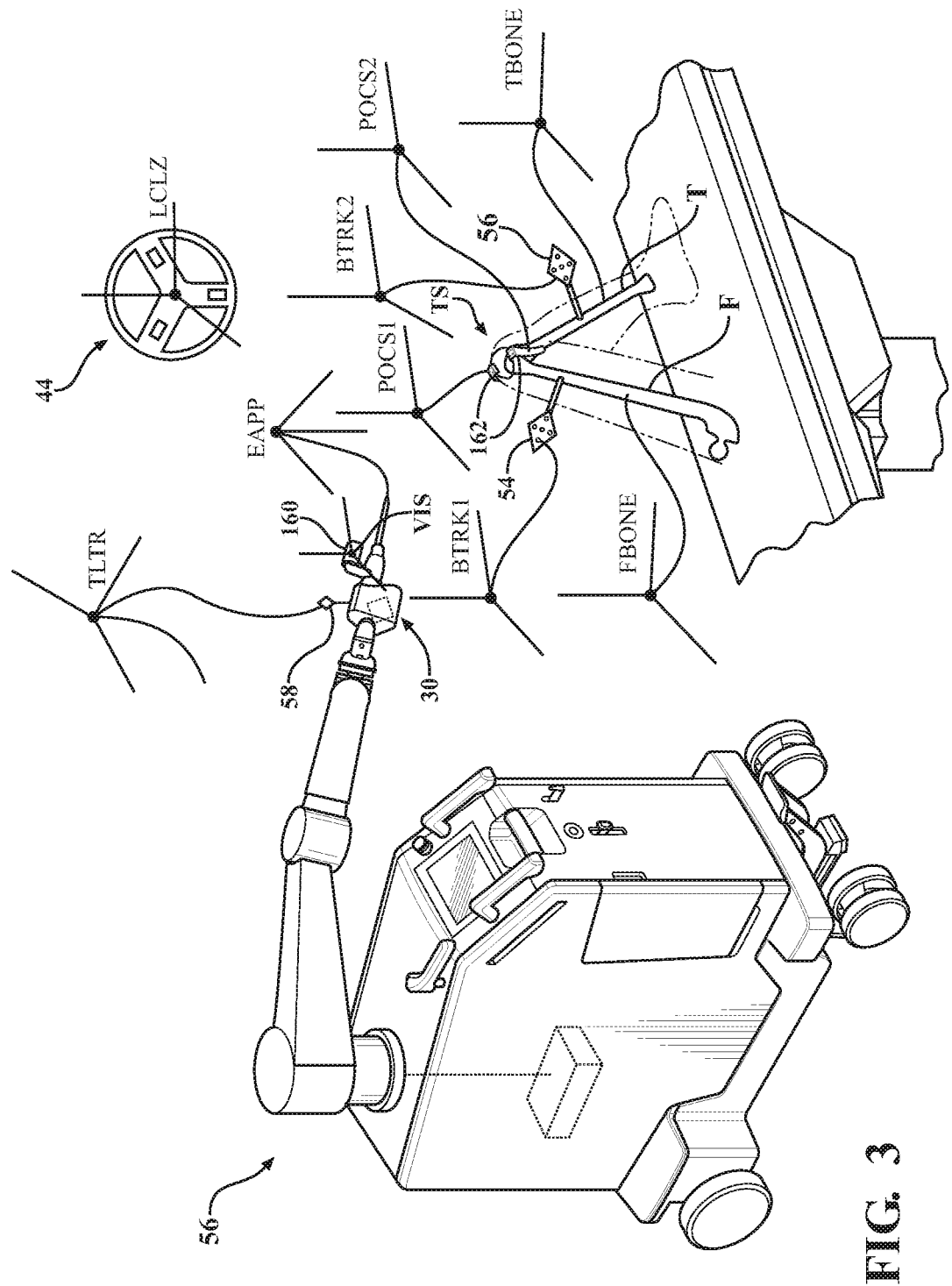
FIG. 3 is a perspective view of coordinate systems used in the robotic surgical system.

Referring to FIG. 3, tracking of objects is generally conducted with reference to a localizer coordinate system LCLZ. The localizer coordinate system LCLZ has an origin and an orientation (a set of x, y, and z axes). During the procedure one goal is to keep the localizer coordinate system LCLZ in a known position. An accelerometer (not shown) mounted to the localizer camera unit 46 may be used to track sudden or unexpected movement of the localizer coordinate system LCLZ, as may occur when the localizer camera unit 46 is inadvertently bumped by surgical personnel.

Each tracker 54, 56, 58, and object being tracked also has its own coordinate system separate from the localizer coordinate system LCLZ. For instance, the trackers 54, 56, 58 have bone tracker coordinate system BTRK1, bone tracker coordinate system BTRK2, and instrument tracker coordinate system TLTR.

In the embodiment shown, the guidance station 26 monitors the positions of the femur F and tibia T of the patient by monitoring the position of bone trackers 54, 56 firmly attached to bone. Femur coordinate system is FBONE and tibia coordinate system is TBONE, which are the coordinate systems of the bones to which the bone trackers 54, 56 are firmly attached.

The target sites to be treated by the surgical instrument 30 are defined by virtual objects. In the embodiment shown, the femur target site TS is associated with the femur F. Of course, several other target sites, such as a target site for the tibia T, are also possible, with each being defined by its own separate virtual object. The virtual objects representing the target sites are pre-operatively set by the user to define volumes of material to be treated, trajectories for the surgical instrument 30, planes to be cut by the surgical instrument 30, bores to be drilled, and the like. In the embodiment shown, a virtual object VB (see FIG. 9) defines the volume of material to be removed from the femur F. In some cases, the virtual objects are set or re-set intraoperatively, i.e., during the surgical procedure. It should be appreciated that although the description set forth herein relates to orthopedic surgical procedures, the systems and methods described herein are likewise suitable for any type of surgical procedure.

Prior to the start of the procedure, pre-operative images of the anatomy of interest are generated, such as pre-operative images of the femur F and tibia T (or of other tissues or structures in other embodiments). These images may be based on MRI scans, radiological scans or computed tomography (CT) scans of the patient's anatomy. These images are used to develop virtual models of anatomy of interest, such as virtual models of the femur F and tibia T and/or other anatomy to be treated by the surgical instrument 30. Such virtual models can also be created intraoperatively, such as by capturing points on a surface of the femur F and tibia T and/or other anatomy to be treated using a navigation pointer or other suitable device. The points are then compiled and gaps between the points filled to generate the virtual model. Such point collection can also be combined with a generic bone model to enable morphing of the generic bone model to better match the anatomy of interest.

Often the virtual models are 3-D models that comprise data representing the entire anatomy being treated or at least a portion of the anatomy to be treated and data representing the virtual objects that define the target sites. In the embodiment shown, a virtual model VM of the femur is a 3-D model comprising model data that represents a portion of the femur F and the virtual object VB (see FIG. 9). The virtual object VB defines the target site TS and the volume of material to be removed from the femur F during the surgical procedure. The virtual objects may be defined within the virtual models and may be represented as mesh surfaces, constructive solid geometries (CSG), voxels, or using other virtual object representation techniques.

The pre-operative images and/or the virtual models are mapped to the femur coordinate system FBONE and tibia coordinate system TBONE using well known methods in the art. These pre-operative images and/or virtual models are fixed in the femur coordinate system FBONE and tibia coordinate system TBONE. As an alternative to taking pre-operative images, plans for treatment can be developed in the operating room from kinematic studies, bone tracing, and other methods. These same methods could also be used to generate the 3-D virtual models previously described.

During an initial phase of the procedure described herein, the bone trackers 54, 56 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIG. 1), such as disclosed in U.S. Pat. No. 7,725,162 to Malackowski, et al., hereby incorporated by reference, having its own tracker PT (see FIG. 1), may be used to register the femur coordinate system FBONE and tibia coordinate system TBONE to the bone tracker coordinate systems BTRK1 and BTRK2, respectively. Given the fixed relationship between the bones and their trackers 54, 56, positions and orientations of the femur F and tibia T in the femur coordinate system FBONE and tibia coordinate system TBONE can be transformed to the bone tracker coordinate systems BTRK1 and BTRK2 so the localizer camera unit 46 is able to track the femur F and tibia T by tracking the trackers 54, 56. These pose-describing data are stored in memory integral with both the manipulator controller 64 and the navigation processor 62.

The treatment end of the surgical instrument 30 (also referred to as a distal end of an energy applicator) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with manipulator controller 64 and navigation processor 62.

Referring to FIG. 2, a localization engine 100 is a software module that can be considered part of the navigation computer 34. Components of the localization engine 100 run on navigation processor 62. The localization engine 100 may run on the manipulator controller 64 and/or the navigation processor 62.

Localization engine 100 receives as inputs the optically-based signals from the localizer camera controller 52 and, in some embodiments, the non-optically based signals from the tracker controller 61. Based on these signals, localization engine 100 determines the pose of the bone tracker coordinate systems BTRK1 and BTRK2 in the localizer coordinate system LCLZ. Based on the same signals received for the instrument tracker 58, the localization engine 100 determines the pose of the instrument tracker coordinate system TLTR in the localizer coordinate system LCLZ.

The localization engine 100 forwards the signals representative of the poses of trackers 54, 56, 58 to a coordinate transformer 102. Coordinate transformer 102 is a software module that runs on navigation processor 62. Coordinate transformer 102 references the data that defines the relationship between the pre-operative images and/or the virtual models of the patient and the bone trackers 54, 56. Coordinate transformer 102 also stores the data indicating the pose of the treatment end of the surgical instrument 30 relative to the instrument tracker 58. Coordinate transformer 102 also references the data that defines the virtual objects, if separate from the virtual models.

During the procedure, the coordinate transformer 102 receives the data indicating the relative poses of the trackers 54, 56, 58 to the localizer 44. Based on these data and the previously loaded data, the coordinate transformer 102 generates data indicating the relative position and orientation of both the coordinate system EAPP, and the bone coordinate systems, FBONE, TBONE to the localizer coordinate system LCLZ.

As a result, coordinate transformer 102 generates data indicating the position and orientation of the treatment end of the surgical instrument 30 relative to the target sites against which the treatment end is applied. Image signals representative of these data are forwarded to displays 36, 38 enabling the surgeon and staff to view this information. In certain embodiments, other signals representative of these data can be forwarded to the manipulator controller 64 to guide the manipulator 66 and corresponding movement of the surgical instrument 30. Thus, this data also indicates a virtual location of the treatment end of the surgical instrument 30, which may also be modeled as a separate virtual object, e.g., virtual tool object VI, with respect to the other virtual objects.

Referring back to FIG. 1, the guidance station 26 further includes a vision device 72. In the embodiment shown, the vision device is mounted to the surgical instrument 30. In other embodiments, the vision device 72 may be mounted to the robotic arm, such as at a distal end of the robotic arm. The vision device 72 is preferably placed so that it has a field of view of the target sites free from obstructions. The vision device 72 has a vision controller 73 (see FIG. 2) in operative communication with the navigation computer 34. The vision device 72 may also be referred to as an image device or a digital image device. The vision device 72 may comprise a camera 160 that has an outer housing 76 and that supports one or more image sensors 78 (see FIG. 2). The image sensors 78 may be in the form of CMOS sensors or other suitable sensors.

The navigation computer 34 communicates with the vision controller 73 to receive vision data sets of the camera 160 from the vision controller 73. The vision data sets are provided in the vision coordinate system VIS (see FIG. 3). The vision data sets may be sets of data points in the vision coordinate system VIS captured by the camera 160 as the camera 160 moves relative to the patient. These data points are defined by x, y, z coordinates. The data points can be saved or stored as a vision data file.

Figure 4:
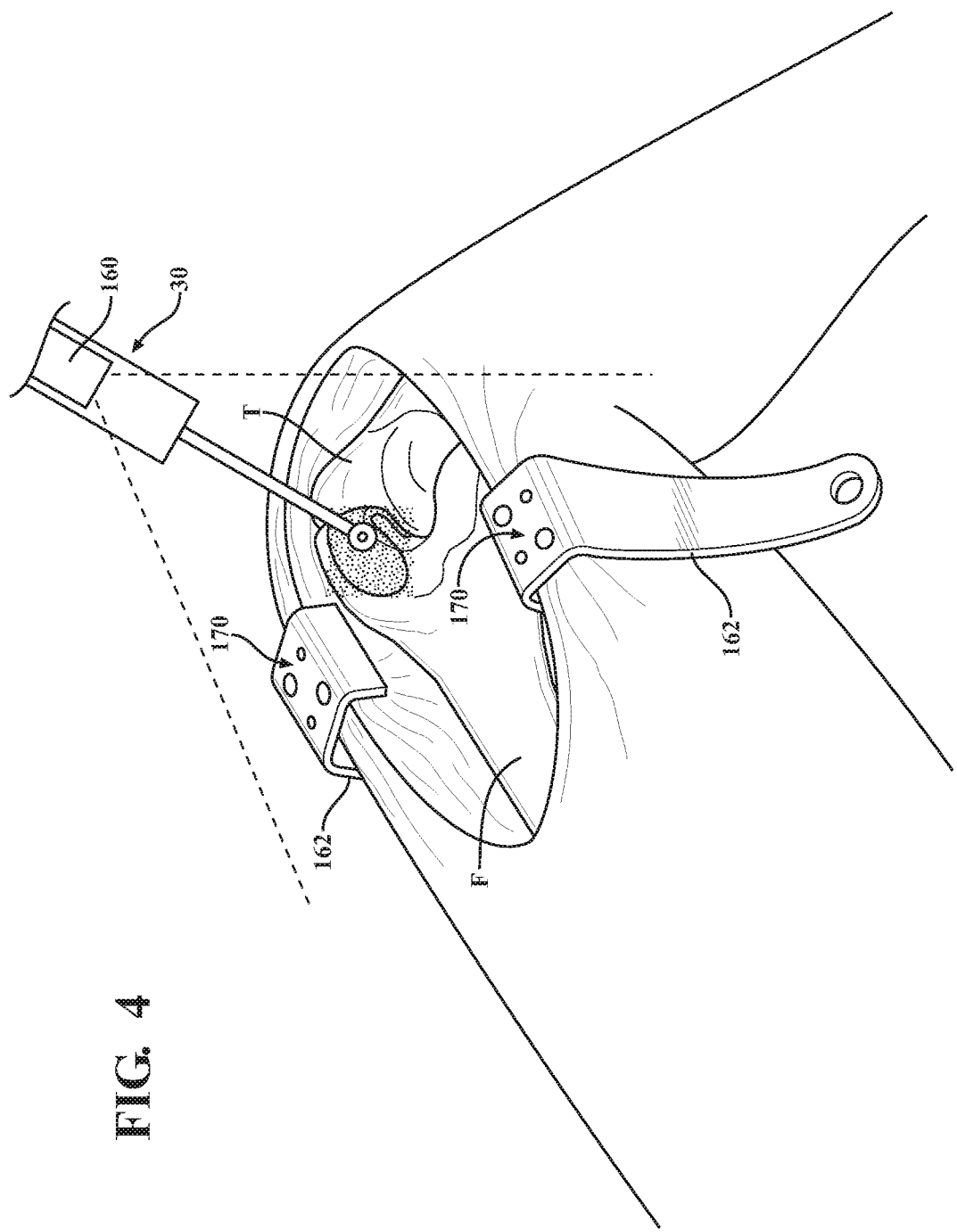
FIG. 4 is an illustration of a surgical site with physical objects being viewed by the vision device.

As shown in FIG. 4, physical objects, other than the femur F, tibia T, and the surgical instrument 30, are present near the target site. Such objects may comprise retractors, irrigation/suction tools, surgical guides, skin around the incision, or other types of physical objects. In the embodiment described herein, the navigation computer 34 and/or manipulator controller 64 identifies and tracks these physical objects so the system 20 can determine the relative positions of the surgical instrument 30, the femur F, the tibia T, and all the physical objects near the target sites, e.g., so the physical objects can be avoided by the surgical instrument 30 during the surgical procedure. In other embodiments, it may be desirable to identify and track the physical objects so that the surgical instrument 30 can engage one or ore of the physical objects in certain situations, such as when the physical objects are tool guides. For purposes of illustration, the physical objects shown are retractors 162.

Referring to FIG. 4, each of the physical objects include multiple features that define a feature set 170 so that the physical objects can be identified and tracked during the surgical procedures by the navigation computer 34 and/or the manipulator controller 64 via the camera 160. The feature set 170 comprises multiple features that are identifiable in the vision data sets taken by the camera 160. For identification purposes, pattern recognition capabilities can be provided by the navigation computer 34 and/or manipulator controller 64. The system 20 has prior knowledge of the arrangement, coding or other characteristics of the features to be detected.

One or more of the features ay be active markings (e.g., emitting radiation to be detected by the camera 160). Additionally, or in the alternative, one or more of the features may be passive markings. Passive markings may have reflecting or non-reflecting properties. Passive markings may be realized by printing, stickers, etc., on any rigid (e.g., planar) or flexible substrate of the physical object (e.g., on a patient's skin surrounding or adjacent to the incision or other location). The features may also be defined by coatings on the surface of the physical object or surface roughness created in the physical object. The system 20 has prior knowledge of the features (e.g., in the form of calibration information). The prior knowledge may relate to one or more of a feature coding scheme and positions of the features relative to each other for several different types of physical objects. Features known prior may, for example, be passive markings stamped or printed on a substrate of the physical object, or alternatively, active markings. In the case of using printed stickers or other passive markings surrounding the incision, the prior known features may be understood to be placed in a ring-shape or other location suitably understood to be associated with the incision opening so that the instrument 30 can be controlled to avoid the skin and other tissue surrounding the opening.

The camera 160 is configured to acquire vision data sets from two or more different perspectives so that each vision data set includes at least some of the features of the feature set 170. Movement of the camera 160 results from movement of the robotic device and/or instrument 30 relative to the patient when collecting the vision data sets. This movement could be caused by manual manipulation of the robotic device and/or the instrument 30 or autonomous movement of the robotic device and/or the instrument 30. As an example, the camera 160 may be realized as a video camera capable of providing the vision data sets in the form of a continuous video data stream (e.g., as video frames). In one variant, the camera 160 is rigidly mounted to the instrument 30 such that the camera 160 can be moved together with h instrument 30 by the robotic device during autonomous movement of the robotic device. in other variants, the camera 160 is rigidly mounted to the instrument 160 to be moved with the instrument 30 via manual manipulation of the robotic device and/or the instrument 30. When mounted to the surgical instrument 30, the camera 160 has a field of view that includes the physical objects and a patient surface targeted by the surgical instrument 30. As an example, when the surgical instrument 30 has a longitudinal axis directed towards the patient, the field of view may extend along the longitudinal axis of the surgical instrument 30.

It should be appreciated that by integrating the camera 160 into the surgical instrument 30, the vision coordinate system VIS of the camera 160 can be easily calibrated to the instrument tracker coordinate system TLTR. This calibration can occur during manufacturing, e.g., via calibration data determined during manufacture, or can be calibrated before the procedure begins using conventional calibration methods. Accordingly, the pose of the vision coordinate system VIS relative to the localizer coordinate system LCLZ can be determined based on the transformation methods described above and use of the instrument tracker 58 associated with the surgical instrument 30. As a result, the vision coordinate system VIS can also be transformed to the localizer coordinate system LCLZ or vice versa. The pose-describing data are stored in memory integral with manipulator controller 64 and navigation processor 62.

In other embodiments, such as those in which the camera 160 is mounted to the robotic device instead of the surgical instrument 30, the camera 160 may have a vision device tracker (not shown) rigidly mounted to the housing 76 to establish a relationship between the vision coordinate system VIS and the localizer coordinate system LCLZ. For instance, using preloaded data defining a relationship between the vision device tracker's coordinate system and the vision coordinate system VIS, the coordinate transformer 102, based on the position and orientation of the vision device tracker in the localizer coordinate system LCLZ, could transform the vision coordinate system VIS to the localizer coordinate system LCLZ. Alternatively, if the robotic device is separately being tracked in the localizer coordinate system LCLZ, such as via joint encoders and a robot base tracker (not shown) attached to a base of the robotic device, the camera 160 can be associated with the robot base tracker (e.g., via a calibration step) thereby eliminating the need for a separate tracker on the camera 160. As long as the base of the robotic device does not move, and the robot base tracker is visible, the localizer 44 can determine a position and orientation of the camera 160.

The navigation computer 34 may be configured to store the vision data sets received from the camera 160 in external or internal storage. As mentioned above, those vision data sets may be received in the form of a video data stream that is at least temporarily stored for being processed by the navigation processor 62. Such processing may, for example, include pattern recognition to identify (e.g., locate and decode) one or more of the features in the received vision data sets.

In one embodiment, the navigation processor 62, using pattern recognition techniques, first identifies multiple features in the vision data sets and determines their coordinates (e.g., in the form of key point coordinates) in the vision coordinate system VIS. A projection model of the camera 160, stored as calibration data, may be used to determine the position of the camera 160 relative to one or more features identified in the vision data sets provided by the camera 160 (See, e.g., United States Patent Application Publication No. 2008/0208041A1, hereby incorporated herein by reference). The transformation parameters underlying a particular projection model may be provided by the respective camera manufacturer or by a distributer of the system 20. They could also be estimated with an on-site calibration fixture or be standardized for a particular camera type. In certain implementations, the transformation parameters may be provided via a suitable interface by the camera 160 itself (e.g., in real-time dependent on a currently selected zoom level).

Also provided as calibration data, for example in the internal storage of the navigation computer 34, is information pertaining to the feature sets 170. Such information may include relative positions of the features and/or any applied coding scheme of the features. Based on the known feature relative positions and the (projected) feature relative positions in a vision data set (e.g., image) taken by the camera 160 (i.e., in the associated vision coordinate system VIS), transformation parameters of a further transformation can be determined (e.g., in real-time) by a perspective back-projection from the corresponding vision coordinate system VIS towards any reference system in which the feature coordinates are provided, such as a physical object coordinate system POCS of a physical object of interest (see FIG. 3). This is indicated by a transformation T1 for the camera 160. The transformation parameters of the transformation T1 for the camera 160 are calculated by solving the following equation system for each individual feature j:

$$M_{j,160} = T2 \cdot T1^{-1} \cdot M_{j,cal},$$

$M_{j,160}$ is the imaged feature j in the vision data set (e.g., video frame) of the camera 160 with coordinates relative to the vision coordinate system VIS. $M_{j,cal}$ is provided as calibration data and indicative of (e.g., a key point of) the feature j with coordinates relative to the physical object coordinate system POCS, and a second transformation T2 designates the transformation parameters between the camera 160 and its associated vision coordinate system VIS.

Figure 5:
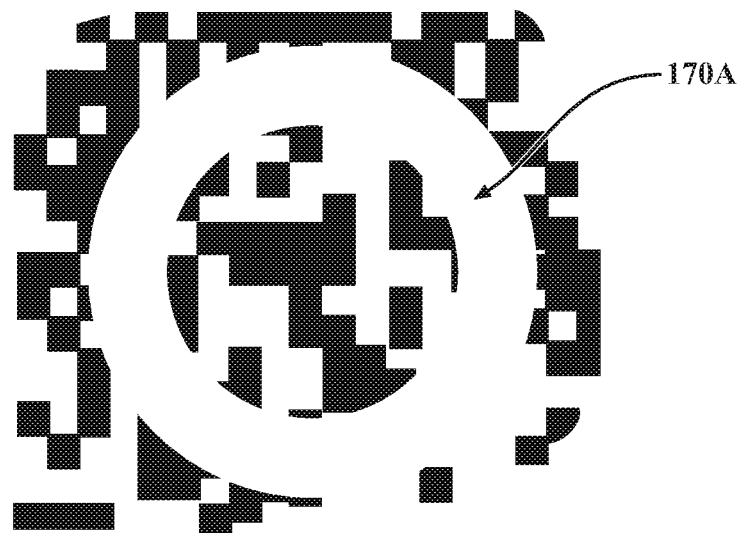
FIG. 5 is an example of a feature on a physical object.
Figure 6:
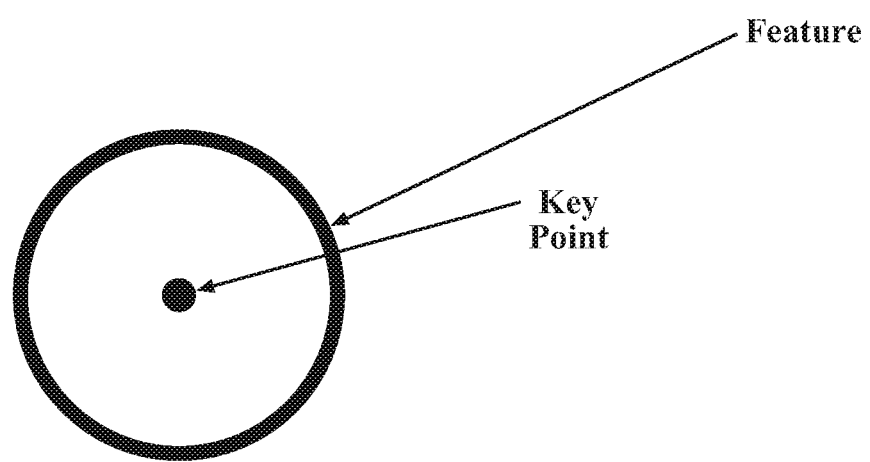
FIG. 6 is another example of a feature on the physical object.
Figure 7:
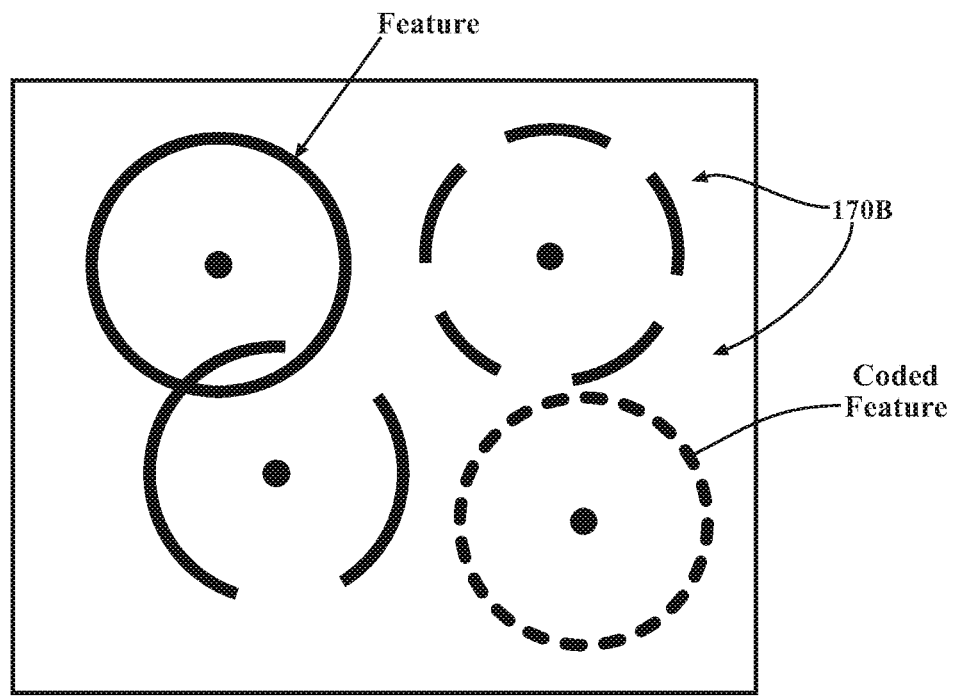
FIG. 7 is an example of a group of features, including coded features.

It should be noted that the perspective back-projection described above is sometimes referred to as camera pose estimation, or performed in connection with camera pose estimation. In the embodiment shown in FIG. 4, the individual features are symbolized by black points. Multiple coded features could also be used. Each feature may have a two-dimensional extension which includes a unique, extended QR-type coding (which permits an overlap of individual features). In FIG. 5, an individual extended feature 170A is graphically illustrated to lie within a white ring, wherein the center of the ring defines a feature key point. Generally, each extended feature may define such a specific key point, or a center, that indicates a position, or the coordinates, of the feature. In computer vision, the term feature is also referred to as the description of a key point surrounding (i.e., of a feature extension). FIG. 6 schematically illustrates the key point concept for an extended feature in the exemplary form of a ring. It will be appreciated that the key point concept can readily be extended to the feature type of FIG. 5. It will be appreciated that in alternative embodiments the individual features could be defined and coded otherwise. For instance, the rings could be dashed with different numbers of dashes or combinations of dashes and dots, as shown by the features 170B in FIG. 7. As another example, colored-coded circles or dots may be used. In certain implementations, individual features may be grouped on the physical object within a small area that forms a flat (i.e., planar) surface. The relative positions of individual features as well as their coding scheme (that allows differentiating individual features) may be stored as calibration data.

Figure 8:
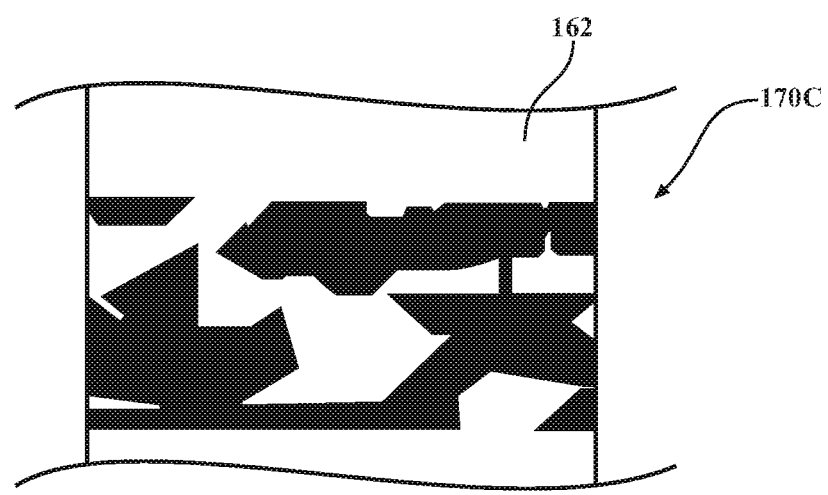
FIG. 8 is an example of a feature set, including coded features.

In the present embodiment, the physical object coordinate system POCS is defined, or spanned, by the features 170C (in the form of combinations of black and white areas) provided on the two-dimensional surface of the physical object, as shown in FIG. 8. This means that once the features (also referred to as tracker features) defined on the surface of the physical object have been identified and decoded in the vision data sets received from the camera 160, the physical object coordinate system POCS can be determined, together with the coordinates of those features within the physical object coordinate system POCS. The system 20 will typically also have prior knowledge (in the form of calibration data) regarding the relative positions and the codings of the features provided on the physical object.

The tracker features may be unique and/or coded so that the navigation computer 34 and/or manipulator controller 64 can identify the physical object or information relating to the physical object based on the features, such as by pattern recognition of the features or by virtue of coded information in the features. Such information may comprise one or more of physical object identification, physical object type, physical object size, physical object dimensions, physical object serial number, or physical object manufacturer.

Figure 9:
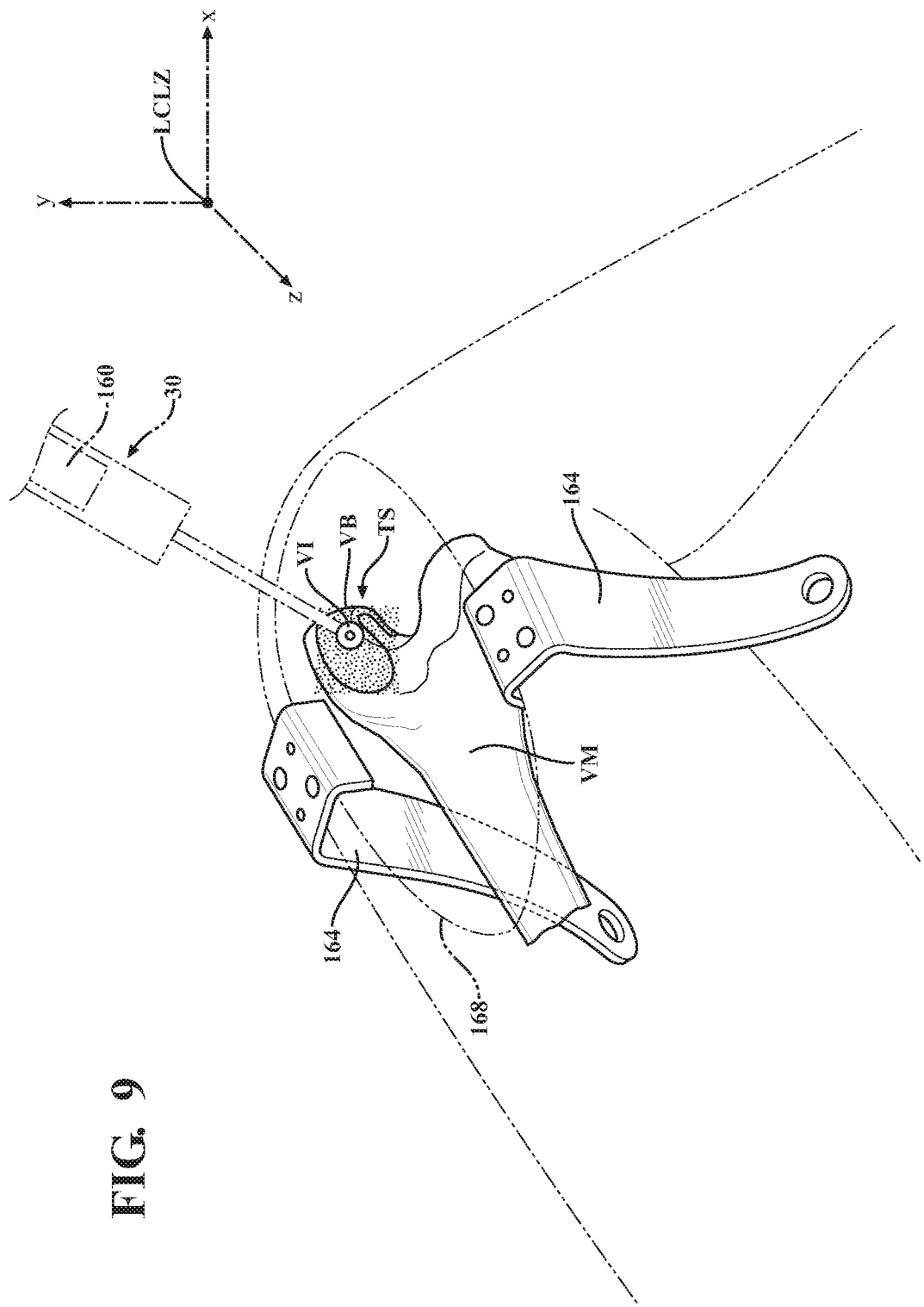
FIG. 9 is an illustration of virtual objects associated with the physical object.

Referring to FIG. 9, once the physical object is identified, the navigation computer 34 and/or manipulator controller 64 can retrieve from memory, such as from a database of physical objects, a virtual object 164 associated with the physical object in the physical object coordinate system POCS. Alternatively, the features on the physical object may be coded with information relating to the virtual object such as virtual object identification, virtual object type, virtual object size, or virtual object dimensions. For instance, the database of physical objects stored in the navigation computer 34 may comprise physical objects made by several different manufacturers, of several different types, and several different sizes and configurations. The information coded in the features enables the navigation computer 34 to identify specific details about the physical objects viewed in the vision data sets based on the features of that particular physical object, and also retrieve a specific virtual object associated with that physical object. Thus, for instance, if the physical object is identified to be a retractor of a certain size, the associated virtual object may be of a comparable size.

The virtual object 164, via transformation of the feature coordinates in the physical object coordinate system PACS to the vision coordinate system VIS, can also be transformed to the vision coordinate system VIS. The virtual object 164 can be further transformed to the localizer coordinate system LCLZ (as shown in FIG. 9) so that movement of the surgical instrument 30 can be tracked with respect to the virtual object 164. In this regard, the virtual object 164 can be predefined with respect to the feature coordinates. For instance, in the case of retractors, the virtual objects are predefined during manufacture as three-dimensional models of the retractors with associated model data established relative to the features on the retractors so that the position and orientation of the virtual object is known in the physical object coordinate system POCS.

In alternative embodiments, prior knowledge of the virtual object 164 with respect to the physical object is not needed, as the user could define the virtual object 164 using a navigation pointer or using the surgical instrument 30 since the coordinates of the surgical instrument 30 are known. As a result, the user would be able to define a "no-fly" zone, e.g., point, line, volume, area, etc., by simply outlining the zone with the navigation pointer. This traced/outlined zone would establish the virtual object 164 with respect to the feature(s) being used to track the virtual object 164.

The virtual object 164 may define a volume or region, such as the space occupied by the retractors 162, to be avoided during the surgery. As shown in FIG. 9, the virtual object 164 may be defined outside of the target site TS in the localizer coordinate system LCLZ. In other embodiments, portions of the virtual object may be present inside the target site TS. The virtual object 164 can be processed by the navigation processor 62 to be displayed to the user on the displays 36, 38 so that the user can visualize a position and orientation of the surgical instrument 30 relative to the target site TS and the virtual objects 164, e.g., of the retractors 162. In some cases, the virtual objects 164 comprise one or more of a three dimensional model, a two dimensional surface, a point cloud, a voxelized volume, a surface mesh, a plane, a line, or a single point.

It should be noted that the physical objects, such as the retractors 162, may move relative to the target site TS during the surgical procedure owing to the elastic and/or flexible nature of some of the tissues near the target site TS. As a result, the system 20 periodically refreshes the determined poses of the virtual objects, e.g., the virtual objects 164 associated with the retractors 162, in the localizer coordinate system LCLZ or other coordinate system of interest. This update of the pose of the virtual objects may occur at the same rate as the poses of the trackers 54, 56, 58 are being updated by the localizer, at the same rate as each new commanded position of the surgical instrument along a tool path is being calculated by the manipulator controller 64, or at any other suitable rate. In some cases, updating the poses of some physical objects can be slower than others. For instance, updating the locations of the retractors 162 may occur less frequently than updating the location of the surgical instrument 30 relative to the target site TS, since knowledge of the location of the surgical instrument 30 may be more critical in certain cases.

In some embodiments, virtual objects may be created based on the locations of multiple physical objects. For instance, a virtual incision 168 (see FIG. 9) may be defined by the location of two or more retractors 162, as shown. The virtual incision 168, in this case, may be a virtual opening having a boundary outlined by the retractors 162. As such, as the retractors 162 are adjusted, the virtual incision 168 may change configuration. In other words, the virtual incision 168 may be dynamic and may change shape, but with the navigation techniques described herein, the virtual incision 168 can be continuously updated with each new vision data set so that the instrument 30 is able to avoid the physical object or boundaries defined by virtual objects associated with such physical objects during the surgical procedure regardless of changes near the target site TS.

The virtual object may define a volume or boundary to be avoided and therefore create a "no-fly" zone in which the treatment end of the surgical instrument 30 is prevented from entering. The "no-fly" zone may be associated with sensitive anatomical structures, rigid structures, soft tissue and bone to be preserved, other tools, and the like located near the target sites. Owing to the knowledge of the location of the virtual objects in the localizer coordinate system LCLZ, or other common coordinate system, when the manipulator 66 operates in an autonomous mode, the manipulator 66 is able to control positioning of the surgical instrument 30 to avoid the virtual objects and thereby avoid sensitive anatomical structures, rigid structures, soft tissue and bone to be preserved, other tools, and the like, located near the target sites. During manual manipulation of the robotic device and/or the instrument 30, the "no-fly" zones would act as haptic boundaries that provide haptic feedback to the user to prevent the user from entering the "no-fly" zones with the instrument 30. For instance, when the physical objects are retractors, each of the physical objects has a virtual object associated therewith in the form of virtual three-dimensional models of the retractors. The physical objects, by virtue of being tracked by the camera 160, can be avoided by tracking movement of the treatment end of the surgical instrument 30 relative to the retractors. The manipulator controller 64 can then adjust its tool path or stop movement of the surgical instrument 30 should one of the retractors be positioned within the tool path. Alternatively, in the manual mode of operation, the manipulator controller 64 can limit/stop movement that would otherwise cause a collision of the robotic device and/or the instrument 30 with one of the retractors, such as by actively actuating one or more joint motors, brakes, or the like, to generate haptic feedback to the user in the event of the instrument 30 reaching the "no-fly" zone during manual manipulation.

Similarly, the navigation system could warn the user that the physical object, such as one of the retractors, interferes with the planned tool path and advise the user to move the physical object.

Figure 10:
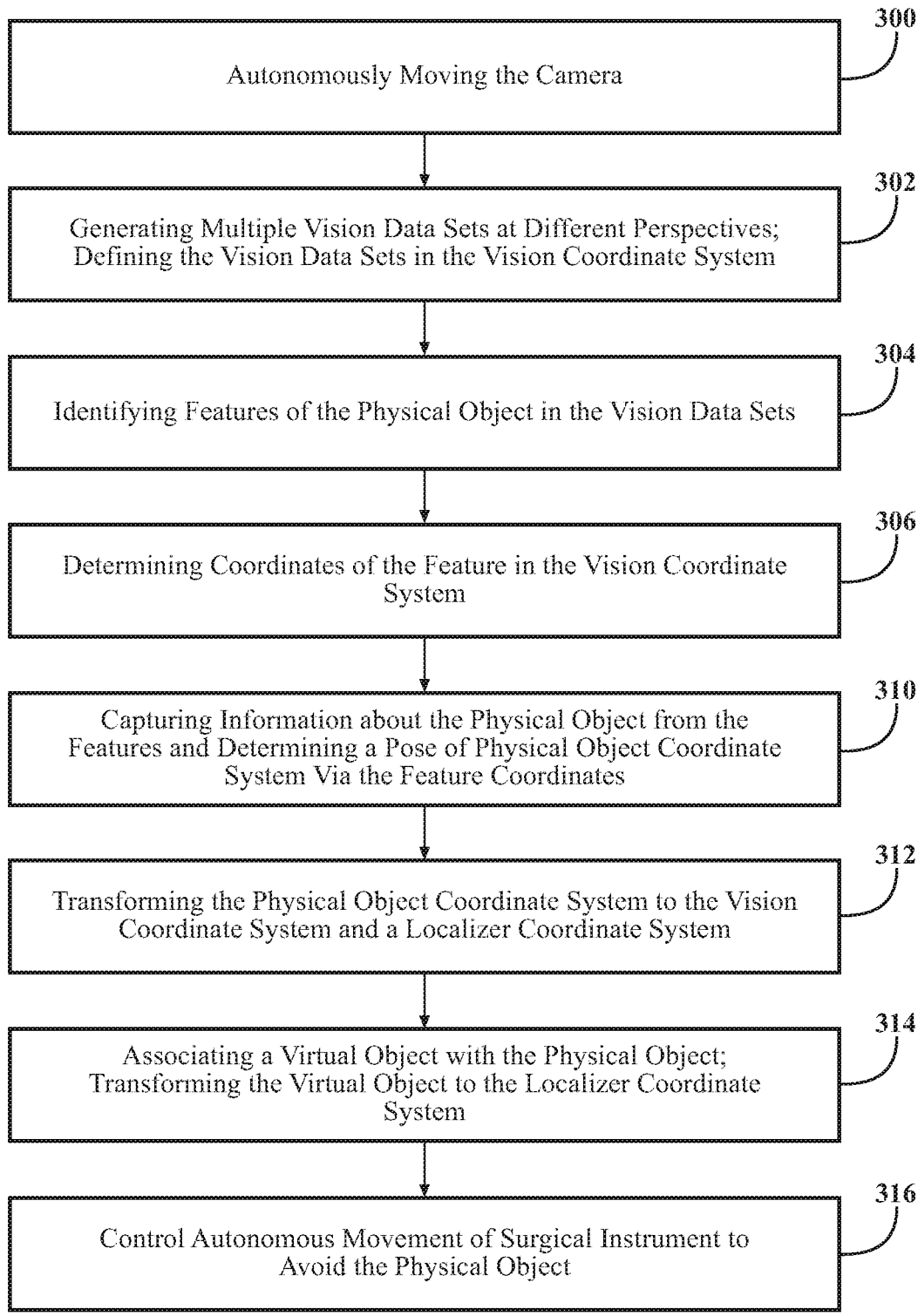
FIG. 10 is a flow chart of steps carried out by a method.

Referring to FIG. 10, one embodiment of a method for tracking the physical object with respect to the target site utilizes the robotic device in the autonomous mode. In a first step 300, the camera 160 is moved relative to the physical objects near the target site by virtue of the surgical instrument 30 being moved autonomously relative to the target site to treat the target site. The camera 160 is also moving autonomously relative to the physical object and generates vision data sets from multiple perspectives of the physical object in step 302 (although a single perspective may be sufficient). The vision data sets are defined in the vision coordinate system VIS.

One or more features, preferably at least three or four features, are identified in the vision data sets in step 304. The features may be grouped in a feature set 170 so that the camera 160 is able to determine feature coordinates of each of the features in the vision coordinate system VIS in step 306. The features, or other visual identifiers, which are coded in certain embodiments, are recognized using pattern recognition techniques. Based on this recognition, information regarding the physical object can be captured by the navigation computer 34 and/or manipulator controller 64 in step 310. This information can include, for instance, a position and orientation of a physical object coordinate system POCS relative to the feature coordinates.

In step 312, the physical object coordinate system POCS can then be transformed to the vision coordinate system VIS and to the localizer coordinate system LCLZ via the coordinate transformer 102. In step 314, a virtual object is associated with the physical object. The virtual object is defined in the physical object coordinate system POCS is retrieved from memory and, owing to the transformation, is defined with respect to the vision coordinate system VIS and subsequently to the localizer coordinate system LCLZ. In step 316, the manipulator controller 64 controls autonomous movement of the manipulator 66 and the surgical instrument 30 attached thereto so that the surgical instrument 30 avoids the physical object or other constraint defined by the physical object.

It should be appreciated that although the virtual object associated with the physical object is transformed to the localizer coordinate system LCLZ, to be tracked relative to the treatment end of the surgical instrument 30 and to the target site, any common coordinate system could be used to track relative movement and poses of the surgical instrument 30, target site, and physical objects, such as the manipulator coordinate system MNPL, or other coordinate system.

As will be appreciated by one skilled in the art, aspects of the present embodiments may take the form of a computer program product embodied in one or more computer readable medium(s) having computer readable program code embodied thereon. Computer software including instructions or code for performing the methodologies described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

In other embodiments, the feature coordinates and models of the physical objects can be determined using one or more of a Structure-from-Motion (SfM) technique, a Simultaneous Localization and Mapping (SLAM) technique and a pose estimation technique. As an example, SLAM may be applied to the feature groups. As a further example, SfM may build feature tracks for individual features (not necessarily feature groups) identifiable in the vision data sets from different perspectives. Triangulation based on different (camera) perspectives may be applied to individual feature tracks. Triangulation may help to reconstruct and, optionally, optimize the feature coordinates in three dimensions (e.g., in the physical object coordinate system).

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A navigation system for tracking a physical object, said navigation system comprising:
   a robotic device;
   an instrument attachable to said robotic device, the instrument being configured to treat tissue at a target site;
   a vision device attached to one of said robotic device or said instrument such that said vision device is movable with said robotic device, said vision device configured to generate vision data sets, wherein said vision data sets are captured from multiple perspectives of the physical object enabled by said vision device being moved in a plurality of degrees of freedom when moving said robotic device, and the physical object being at least one of the target site and an object to be avoided at or near the target site; and
   a computing system in communication with said vision device, said computing system having at least one processor configured to associate a virtual object with the physical object based on one or more features of the physical object identifiable in said vision data sets, wherein the virtual object at least partially defines a virtual boundary utilized to provide a constraint on movement of the instrument relative to the physical object.

2. The navigation system as set forth in claim 1, wherein said vision device comprises a camera.

3. The navigation system as set forth in claim 1, wherein said computing system is configured to track a position and orientation of said vision device at each location of said vision device in which said vision data sets are generated.

4. The navigation system as set forth in claim 1, wherein said computing system is configured to determine an identity of the physical object based on said one or more features of the physical object.

5. The navigation system as set forth in claim 4, wherein said computing system is configured to associate said virtual object with the physical object based on the identity of the physical object.

6. The navigation system as set forth in claim 5, wherein said virtual object comprises one or more of a three dimensional model, a two dimensional surface, a point cloud, a voxelized volume, a surface mesh, a plane, a line, or a single point.

7. The navigation system as set forth in claim 1, wherein said one or more features includes a set of features identifiable in said vision data sets and said computing system is configured to determine a position and orientation of the set of features to establish a position and orientation of a first coordinate system associated with the physical object.

8. The navigation system as set forth in claim 7, wherein said vision device is fixed with respect to said one of said robotic device or said instrument so that said vision data sets are transformable into a second coordinate system of said one of said robotic device or said instrument.

9. The navigation system as set forth in claim 8, wherein said computing system includes a coordinate transformer configured to transform one of said coordinate systems so that said computing system can track movement of said instrument relative to the physical object.

10. The navigation system as set forth in claim 9, wherein said computing system is configured to enable movement of said instrument to treat the tissue at the target site while avoiding the physical object by tracking movement of said instrument with respect to the physical object.

11. The navigation system as set forth in claim 1, wherein said computing system is configured to determine information associated with the physical object based on the one or more features.

12. The navigation system as set forth in claim 11, wherein the information comprises one or more of physical object identification, physical object type, physical object size, physical object dimensions, physical object serial number, physical object manufacturer, virtual object identification, virtual object type, virtual object size, or virtual object dimensions.

13. The navigation system as set forth in claim 1, wherein said virtual object is defined by at least one of a navigation pointer or said instrument.

14. The navigation system as set forth in claim 1, wherein said robotic device is configured to operate in an autonomous mode so that said vision device moves autonomously when said robotic device operates in said autonomous mode.

15. A method for tracking a physical object utilizing a robotic device, an instrument attachable to the robotic device and the instrument being configured to treat tissue at a target site, a vision device, and a computing system having at least one processor, and the physical object being at least one of the target site and an object to be avoided at or near the target site, the method comprising the steps of:
generating vision data sets in response to movement of the vision device resulting from movement of the robotic device, wherein the vision data sets are captured from multiple perspectives of the physical object; and
associating a virtual object with the physical object based on one or more features of the physical object identifiable in the vision data sets, wherein the virtual object defines a virtual boundary utilized for providing a constraint on movement of the instrument relative to the physical object.

16. The method as set forth in claim 15, wherein the vision device comprises a camera.

17. The method as set forth in claim 15, comprising tracking a position and orientation of the vision device at each location of the vision device in which the vision data sets are generated.

18. The method as set forth in claim 15, comprising determining an identity of the physical object based on the one or more features of the physical object.

19. The method as set forth in claim 18, comprising associating the virtual object with the physical object based on the identity of the physical object.

20. The method as set forth in claim 19, wherein the virtual object comprises one or more of a three dimensional model, a two dimensional surface, a point cloud, a voxelized volume, a surface mesh, a plane, a line, or a single point.

21. The method as set forth in claim 15, comprising determining a position and orientation of a set of features identifiable in the vision data sets to establish a position and orientation of a first coordinate system associated with the physical object.

22. The method as set forth in claim 21, comprising transforming the vision data sets into a second coordinate system of one of the robotic device or the instrument.

23. The method as set forth in claim 22, comprising transforming one of the coordinate systems so that the computing system can track movement of the instrument relative to the physical object.

24. The method as set forth in claim 23, comprising enabling movement of the instrument to the treat tissue at the target site while avoiding the physical object by tracking movement of the instrument with respect to the physical object.

25. The method as set forth in claim 15, comprising determining information associated with the physical object based on the one or more features.

26. The method as set forth in claim 25, wherein the information comprises one or more of physical object identification, physical object type, physical object size, physical object dimensions, physical object serial number, physical object manufacturer, virtual object identification, virtual object type, virtual object size, or virtual object dimensions.

27. The method as set forth in claim 15, comprising defining the virtual object with at least one of a navigation pointer or the instrument.

28. The method as set forth in claim 15, comprising autonomously moving the robotic device so that the vision device moves autonomously to capture the vision data sets.

* * * * *